United States Patent [19]

Reynolds

[11] 4,064,741
[45] Dec. 27, 1977

[54] REAL-TIME ULTRASONIC IMAGING SYSTEM

[75] Inventor: Charles A. Reynolds, West Haven, Conn.

[73] Assignee: SmithKline Instruments, Inc., Sunnyvale, Calif.

[21] Appl. No.: 744,081

[22] Filed: Nov. 22, 1976

[51] Int. Cl.² .......................................... G01N 29/04
[52] U.S. Cl. ...................................... 73/620; 340/1 R; 340/5 MP
[58] Field of Search .......................... 73/67.8 S, 67.9; 340/1 R, 5 MP

[56] References Cited

U.S. PATENT DOCUMENTS

| | | | |
|---|---|---|---|
| 3,693,415 | 9/1972 | Whittington | 73/67.8 S X |
| 3,820,387 | 6/1974 | Grabendorfer | 73/67.9 |
| 3,881,466 | 5/1975 | Wilcox | 73/67.8 S X |
| 3,911,730 | 10/1975 | Niklas | 73/67.8 S X |

Primary Examiner—Richard C. Queisser
Assistant Examiner—John P. Beauchamp
Attorney, Agent, or Firm—Ervin B. Steinberg; Philip J. Feig

[57] ABSTRACT

An ultrasonic pulse echo real time imaging system comprises a segmented transducer array formed by a plurality of juxtaposed transducer elements. Successive scans are performed by forming a first predetermined quantity of juxtaposed elements and incrementally shifting said first quantity along said array and subsequently shifting a second quantity of elements along the array, said first and said second quantity being different, for example four and three elements respectively. If the respective quantities are shifted incrementally by one element, the beam axis is stepped by one-half element width only, thereby providing improved image resolution. The image presentation on a cathode ray tube makes use of the interlacing feature, specifically the B-scan presentation line raster responsive to alternate array scans is interlaced.

24 Claims, 3 Drawing Figures

REAL-TIME ULTRASONIC IMAGING SYSTEM

SUMMARY OF THE INVENTION

This invention relates generally to ultrasonic pulse-echo exploration of bodies and structures and more specifically concerns an arrangement for energizing a segmented transducer array for providing improved image resolution in real time continuous imaging systems.

Systems of the type stated above are used extensively in medical applications for providing instantaneous and continuous images of moving anatomic organs and structures, such as the heart or fetus. The system is also useful for providing a 100 percent ultrasonic inspection of workpiece cross-sections in industrial nondestructive testing applications.

The use of segmented transducer arrays of linear or curved shape for ultrasonic scanning is well known. A typical arrangement of this type comprises a quantity of juxtaposed piezoelectric transducer elements disposed in a common housing. Each transducer element is sequentially rendered operative either singly or in combination with other elements forming a group in the array for transmitting an ultrasonic search signal into an object and for subsequently receiving echo responsive signals. The lateral resolution of the array is limited by the center-to-center distance between the elements which, in turn, is dependent upon the size and operating frequency of the elements.

U.S. Pat. No. 3,789,833, issued to N. Bom, entitled "Heart Examination By Means Of Ultrasound Waves", discloses a transducer array of the type stated above, each element of the array being sequentially energized. In U.S. Pat. No. 3,820,387, issued to W. Grabendorfer et al, entitled "Probe System For Ultrasonic Nondestructive Testing"; U.S. Pat. No. 3,881,466, issued to M. H. Wilcox, entitled "Ultrasonic Cross-Sectional Imaging System"; U.S. Pat. No. 3,693,415, entitled "Scanning Ultrasonic Inspection Method and Apparatus", and West German patent publication OS No. 1,948,463, several transducer array systems are disclosed in which a quantity of juxtaposed elements of the array, forming a group, is simultaneously energized and the group is stepped laterally along the array for scanning the object undergoing examination. An alternative arrangement described in U.S. Pat. No. 3,911,730 issued to L. Niklas, entitled "Ultrasonic transducer Probe System", reveals selected elements of an array being simultaneously energized for creating a pattern similar to a Fresnel zone lens. In each instance, the energized element or group of elements is shifted progressively along the array for causing corresponding motion of the axis of the sound beam along the object under examination. The above patents are incorporated herein by reference.

In the described prior art arrangements, the quantity of transducer elements energized and forming a group is maintained constant and the shift along the transducer array is generally in steps of one element. While such arrangements have proven reasonably successful, the increasing use of real-time ultrasound diagnostic techniques has created a demand for improved image resolution and accuracy. The present invention provides a real time scanning system in which the image resolution is improved by effectively shifting the ultrasonic energy beam along the array in steps of only one-half element, i.e. the axis of the acoustic energy beam moves one-half center-to-center distance between two juxtaposed transducer elements.

In a typical prior art arrangements a group comprising a fixed quantity of juxtaposed elements is simultaneously energized and this group is shifted along the array for providing a real time image of the object under test. Each energization results in the "tracing" of a single line on a display. An array of 64 elements, for instance, when energized in four element groups produces a 61-line raster on a cathode ray tube display, see Wilcox supra.

In contrast, the present invention employs a counter for controlling the location of the individual B-scan presentation lines to be traced along one axis of the display. During a first energization (scan) of the 64 elements comprising the array, a group of four elements is simultaneously energized and shifted by one element per energization resulting in a 61-line display as described above. The least significant bit of the counter is maintained in a fixed state for causing each line of the display during the scan to be displaced two lines per energization for tracing alternate lines on the display. After the 61 lines are traced, the counter is reset, causing the least significant bit to change its output state. The elements of the array are then sequentially energized a second time in groups of three elements per group and the received echoes are traced along the previously skipped lines disposed between the traced lines. Therefore, an interlaced display is produced having 123 lines as contrasted with the heretofore used 61-line display. The result is a greatly improved image resolution. Moreover, the axis of the ultrasonic beam from the transducer array is effectively shifted one-half the center-to-center distance juxtaposed transducer elements each time a group of elements is energized for enhancing the resolution and accuracy of the imaging system.

The quantity of elements forming a group is selected by taking into consideration the desired far-field resolution when determining the quantity elements in the large group and considering the desired near-field resolution when determining the quantity of elements in the smaller group. A difference of at least one element per group is necessary to effect a one-half step shift of the beam axis along the array. The repetition rate of the scanning system must be selected for providing a time interval of sufficient duration between successive transmit signals to permit echo responsive signals arising from acoustic discontinuities disposed at a desired maximum distance from the transducer array to be received, and for enabling the system logic and control signals to be processed. In addition, the repetition rate must be sufficiently high for causing the interlaced display to appear as a single picture to the human eye substantially flicker free. In a preferred embodiment, the large group comprises four elements, the smaller group comprises three elements and the repetition rate is 3.5 kilohertz for receiving echoes arising from acoustic discontinuities spaced 20 centimeters from the transducer array. The preferred values can be varied within the constraints set forth above.

A principal object of this invention, therefore, is the provision of an ultrasonic pulse-echo system providing greatly improved image resolution.

Another important object of this invention is the provision of a method and apparatus for energizing a segmented transducer array and effectively shifting the acoustic energy beam axis a lateral distance along the array commensurate with one-half the center-to-center distance between the elements forming the array.

Another object of the invention is the provision of a method and apparatus for energizing a segmented transducer array and effectively shifting the acoustic energy beam axis a lateral distance along the array commensurate with one-half the center-to-center distance between the elements, and displaying the received echo responsive signals on a display in an interlaced manner.

A further object of the invention is the provision of a real time imaging system in which the elements of a transducer array are energized in groups comprising a first number of juxtaposed elements during a first scan of the array and subsequently are energized in groups comprising a second number of elements during a second scan of the array.

A still further object of the invention is the provision of a real time imaging system in which groups of elements of a segmented transducer array having different numbers of elements are alternatively energized, the echo responsive video signals being displayed on the screen of a cathode ray tube in an interlaced manner.

Further and still other objects of the present invention will become more clearly apparent when the description is read in conjunction with the accompanying drawings.

DETAILED DESCRIPTION OF THE INVENTION

Figure 1:
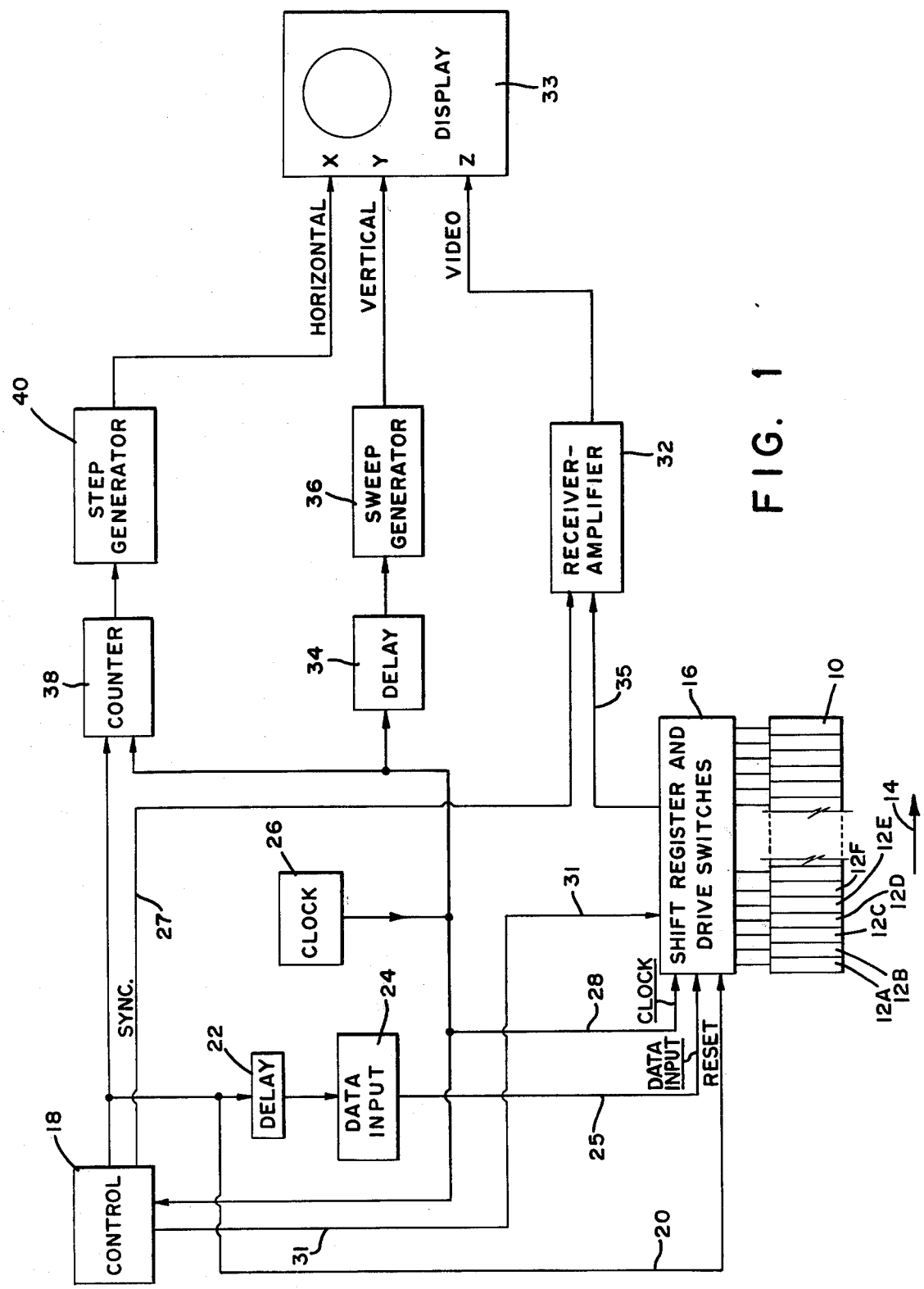
FIG. 1 is a schematic electrical block diagram of a preferred embodiment of the invention.

Referring now to the figures and FIG. 1 in particular, there is shown a segmented transducer array 10 comprising a plurality of juxtaposed transducer elements 12A, 12B, 12C, etc. The construction of the array 10 known in the art, generally comprises a plurality of juxtaposed discrete transducer elements 12A, 12B, 12C, etc., or alternatively comprises a single crystal plate with milled grooves to provide individual elements vibrationally decoupled from juxtaposed elements. Both constructions are described in the book "Ultrasonic Testing of Materials" by J. and H. Krautkramer, Springer-Verlag, New York, Heidelberg and Berlin, 1969, pages 176 to 184. The elements 12A, 12B, 12C etc., are dimensioned to transmit acoustic energy signals at the desired frequency, typically a frequency in the range between 0.5 and 20 megahertz, most commonly in the range between 2.0 and 10.0 megahertz.

Each element 12A, 12B, 12C, etc., of the array 10, responsive to being energized, is adapted to transmit an acoustic energy search signal beam into an object or body to be examined and subsequently to receive echo responsive signals therefrom. In the present embodiment the array 10 is divided into a group of predetermined juxtaposed elements which group is shifted incrementally along the array in the direction of arrow 14. If the group comprises, for instance, four elements 12A, 12B, 12C and 12D as determined by a shift register and drive switches circuit 16, subsequent to the transmission and receipt of acoustic energy signals the group of four elements is shifted one element along the array to include in the next step the elements 12B, 12C, 12D and 12E. The new group transmits and receives acoustic energy signals. The thrid step comprises elements 12C, 12D, 12E and 12F and the cycle is repeated until all juxtaposed four-element groups have been energized in sequence. See Wilcox and Grabendorfer et al. supra. As used hereinafter, the reference numeral 12 refers generally to an element of the array and numeral 12 followed by a letter refers to a specific element, e.g. 12A, 12B, 12C, etc.

The simultaneous transmission by a group of four elements 12 of the array 10 has the same effect as transmitting an acoustic energy search signal into a test object with a single element having a width four times the width of such single element. The shifting of the group along the array in steps of one element advances the acoustic energy beam a distance approximately equal to the center-to-center distance between juxtaposed elements.

The control unit 18 in combination with the data input unit 24 provides during alternate scans of the array 10 the proper signals for conditioning a shift register comprising a portion of shift register and drive switches circuit 16 to its initial condition commensurate with the quantity of elements 12 forming a group. Moreoever, the control unit 18 includes logic circuits including counters for counting the quantity of acoustic energy transmissions made during each scan of the array 10. When the count of transmissions equals the known and previously computed quantity of transmissions necessary to scan the entire array from one end to the other end in groups of predetermined size, i.e. after the last group of elements 12 has been energized, the logic circuits comprising control unit 18 provide a signal along conductor 20 for resetting the shift register and drive switches circuit 16. Concurrently, the same signal is provided to delay 22 (which may be the inherent delay of the logic circuits and need not be a separate circuit) from which delay a further signal to data input unit 24 causes, in turn, a signal along conductor 25 for setting the shift register and drives switches circuit 16 to its new initial condition. The loading of shift registers for subsequent simultaneous energization of predetermined groups of transducer elements is known in the art, see Wilcox, Grabendorfer et al., and Niklas supra. The shift register and drive switches circuit 16 has one output associated with each element 12 of the array 10. The initial condition of the shift register and drive switches circuit 16 causes the first outputs of the shift register corresponding to the predetermined quantity of elements 12 forming a group to be in their high state while the remainder of the outputs from the shift register are in their low state. Upon the receipt of the sequential clock pulses from clock 26 along conductor 28, the high state signals are caused to travel in the direction of arrow 14 along the outputs from the shift register, one step for each clock pulse.

The terms "high state" and "low state" refer to the conventional voltage levels at the output of digital integrated circuits. In an alternative embodiment of the invention the high state and low state may be interchanged when the circuit logic so permits.

A trigger signal provided along conductor 31 from control 18 to shift register and drive switches 16 causes a predetermined group of elements 12 to simultaneously transmit acoustic energy signals into the object to be tested.

The acoustic energy signal upon intercepting an acoustic discontinuity is reflected and a portion of the energy is received by the array 10, particularly the group of elements which transmitted the respective search signal. The received acoustic echo signals are converted into electrical signals by the elements 12 and the electrical signals are coupled via the shift register and drive switches circuit 16 and conductor 35 to a receiver-amplifier 32. The receiver-amplifier 32 transforms the electrical echo responsive signals into video signals for display on the screen of a cathode ray tube 33 in a conventional manner. Moreover, a synchronizing signal from control 18 provided along conductor 27 to receiver-amplifier 32 initiates a time-again compensation circuit which circuit increases the amplification of echo responsive signals arising from acoustic discontinuities disposed farther from the array 10. The construction of such circuits is well known in the art.

The clock pulses from clock 26 are also provided via a delay circuit 34 to a sweep generator 36. The delay 34 in the present embodiment is selected for synchronizing the start of a vertical line trace on the display with the receipt by the array 10 of the workpiece or body entrant surface responsive echo signal. In the case of a contact probe array 10, the delay may be adjusted to approximately zero. The sweep generator 36, responsive to the receipt of the clock signal from delay 34, generates a sawtooth voltage waveform signal for one axis of the deflection circuit of the cathode ray tube 33. In the present embodiment, the vertical scan is controlled by the sweep generator 36 for tracing vertical lines on the display commensurate with each pulse signal supplied to the array 10.

The control unit 18 also provides a signal to the counter circuit 38 for conditioning the counter circuit to count in units of two, either "odd" steps or "even" steps. The output count from counter circuit 38 is provided to the input of a step generator 40 which generator provides direct current signals to the other axis of the deflection system. The counter 38 is programmed so that the direct current output signal from the step generator 40 causes alternate lines on the oscilloscope to be traced.

It will be apparent that by interchanging the X and Y input signals to the display 33, the image will be rotated 90° on the display.

ENERGIZATION OF THE ARRAY

Initially, a pulse from clock 26 activates the control circuit 18 for causing a signal from the control circuit 18 along conductor 20 to reset and zeroize the shift register and drive switches circuit 16. Concurrently, a signal from the control circuit 18 to the data input circuit 24 via delay 22 causes the shift register and drive switches circuit 16 to be conditioned for its initial condition. The data input circuit 24 provides the necessary pulse signals by means of a second, higher frequency clock (not shown) to condition the circuit 16.

In the preferred embodiment, the array 10 comprises 64 elements and each group during a first scan comprises four elements. Therefore, initially the first four outputs of the shift register are in their high state and the remainder of the outputs are in their low state.

Figures 2, 3:
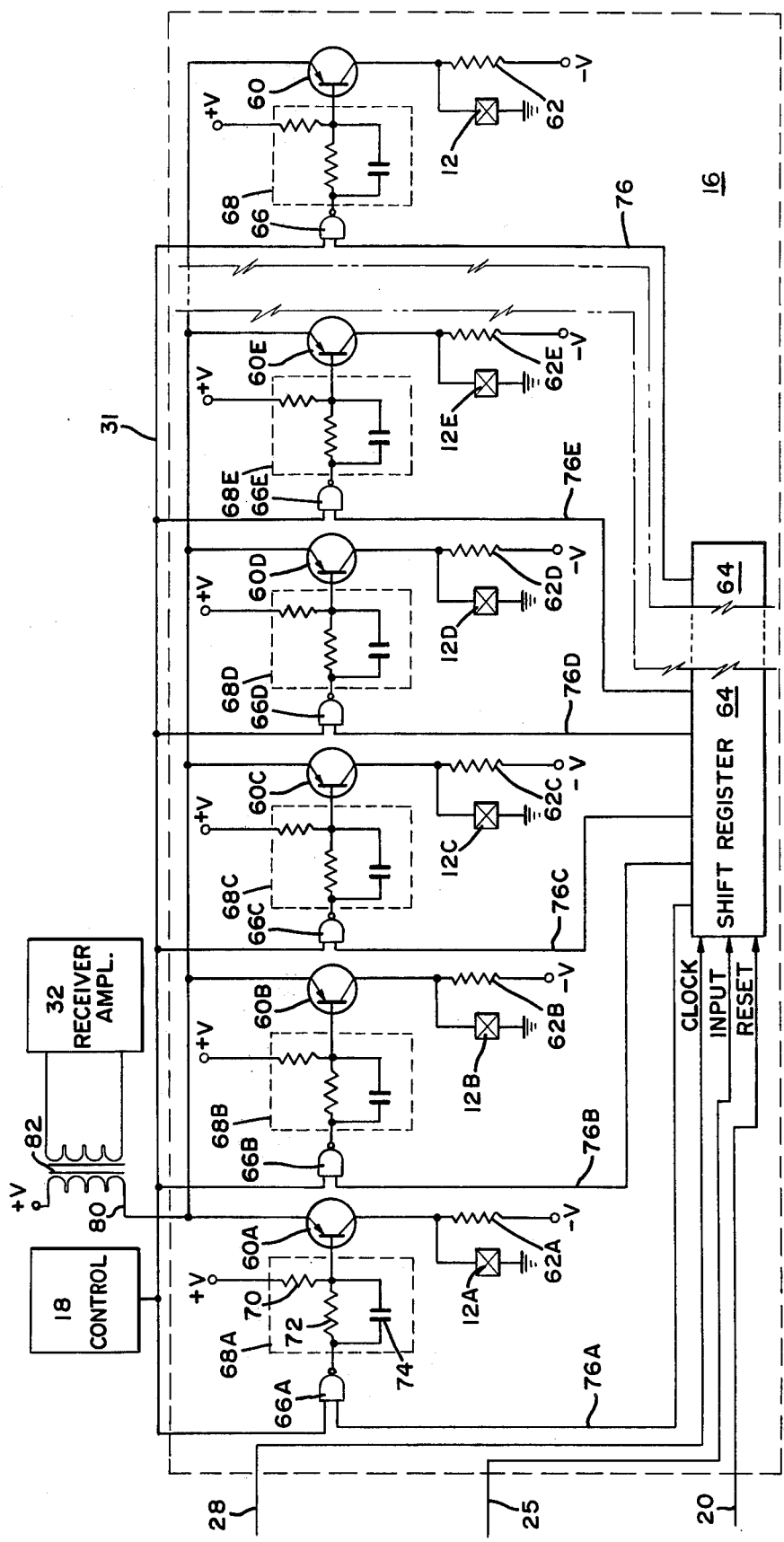
FIG. 2 is a schematic electrical circuit diagram of a portion of the embodiment per FIG. 1.
FIG. 3 is a schematic illustration of a portion of the display obtained per FIG. 1.

As seen in FIG. 2, the control unit 18 provides a trigger pulse to the shift register and drive switches circuit 16. Specifically, the trigger pulse is coupled to one input of respective NAND circuits 66A, 66B, 66C, 66D, etc. Each output of the shift register 64 is connected to the other input of a respective NAND circuit. The output of each NAND circuit 66A, 66B, 66C, etc. is coupled to the input of an associated biasing circuit 68A, 68B, 68C, 68D, etc. As seen in detail with respect to biasing circuit 68A, the biasing circuit includes a resistor 70 connected between a positive potential and the base electrode of transistor 60A, and the parallel connection of a resistor 72 and capacitor 74 connected between the output of NAND circuit 66A and the junction of resistor 70 and the base electrode of transistor 60A. The emitter electrode of each transistor 60A, 60B, 60C, 60D, etc. is coupled to one side of the primary winding of a pulse transformer 82 via conductor 80. The other side of the primary winding is connected to a positive voltage potential. The collector electrode of each of these transsistors is connected to a respective transducer element 12A, 12B, 12C, 12D, etc., which elements comprise the array 10. Resistors 62A, 62B, 62C, 62D, etc., are connected between a negative potential and the junction of a respective transducer element and collector electrode for causing each transducer element 12A, 12B, 12C, 12D, etc., to have a negative voltage across its terminals when the respective element is not transmitting or operative for receiving acoustic energy.

Initially, the first four outputs from shift register 64 along conductors 76A, 76B, 76C and 76D to NAND circuits 66A, 66B, 66C and 66D are in their high state, so that when the trigger pulse along conductor 31 from control 18 to the NAND circuits 66 is simultaneously in its high state, the associated switches 60A, 60B, 60C and 60D are rendered conductive. The conductive switches couple the positive potential at the primary winding of transformer 82 to the respective transducer elements 12A, 12B, 12C and 12D, thereby causing a voltage pulse to be manifest across the respective elements. The presence of a voltage pulse of sufficient amplitude and rise time across the elements 12A, 12B, 12C and 12D causes these elements to simultaneously transmit acoustic energy into the test object. Echo responsive electrical signals arising from the object under test are, in turn, conducted from the respective elements through the conductive switches and conductor 80 (FIG. 2) to the receiver-amplifier 32. By virtue of the common conductor 80 and tranformer 82 the echo responsive electrical signals received by the previously energized elements are summed when conducted to the receiver-amplifier 32.

As stated above, a synchronization signal along conductor 27 to receiver-amplifier 32 initiates a time-gain compensation circuit for providing greater gain for echo responsive signals originating from acoustic discontinuities distanced farther away from the entrant surface of the test object.

Upon receipt of the next clock pulse, the high state outputs of shift register 64 become manifest along conductors 76B, 76C, 76D and 76E. At the next occurrence of a trigger pulse along conductor 31, the four elements 12B, 12C, 12D and 12E transmit and receive acoustic energy signals. The process is repeated until successively each group of four elements along the array 10 has been energized.

In the present example there are 61 combinations of four element groups in the 64 element array. After the sixty-first transmission of acoustic energy is counted by a counter in control unit 18, the shift register 64 is zeroized and a signal from the control 18 to data input 24 via delay 22 causes a second predetermined quantity of outputs from the circuit 64 to be in the high state, thereby defining the quantity of elements in a group during a second scan of the array 10. In the preferred embodiment, three such outputs from the shift register 64 are caused to be in the high state. The above described energizing cycle is repeated, activating concurrently three elements until the elements 12 in the array 10 have been energized three at a time, typically 62 additional transmissions. After a counter in the control unit 18 counts 62 transmissions of acoustic energy the cycle repeats, starting again with groups of four elements.

It will be apparent that in the circuit per FIG. 2, all switches 60 not rendered conductive by shift register circuit 64 and control 18 during a respective pulse signal remain non-conductive and the associated element 12 neither transmits an ultrasonic search signal nor responds to echo responsive signals.

After energizing the array three elements at a time, the cycle is repeated with each successive array scan alternating between four and three element groups. The effect of this type of energization pattern is to shift the axis of the transmitted acoustic energy beam one-half the center-to-center distance between two juxtaposed elements. In the prior art the beam axis is shifted by a distance equal to the center-to-center distance between two juxtaposed elements. It will be apparent therefore, that the invention described herein provides improved resolution over the heretofore known systems.

IMAGING

The display 33 uses an interlacing technique for displaying in a B-scan format the information received responsive to each transmission of acoustic energy into the test object. During scanning of the four element group, for instance, the least significant bit of counter 38 is in its high state responsive to a signal from control unit 18. The output of counter 38 responsive to clock pulses from clock 26 is stepped in intervals of two counts, e.g. 1, 3, 5, 7, etc. The step generator 40 converts these signals to direct current signals for shifting the trace (line raster) on the cathode ray tube to alternate lines 42, 46, 50, etc., as shown in FIG. 3.

Concurrently, sweep generator 36 provides sawtooth waveform voltage signals causing the cathode ray tube to display an image of the test object respective raster lines 42, 46, 50, etc., responsive to video signals received from receiver-amplifier 32.

During alternate scans of the array 10, when three element groups are energized, the least significant bit in counter 38, responsive to a signal from the control circuit 18, is in its low state. The output signals from counter 38 is again stepped in intervals of two, but during this sequence the counts are 2, 4, 6, 8, etc. The step generator 40 converts these signals into direct current signals for shifting the trace on the cathode ray tube to the alternate, interlaced lines 44, 48, 52, etc., per FIG. 3.

The imaging cycles repeat responsive to the signals from the control circuit 18 for updating the presentation on the cathode ray tube 33. The trace rate and update rate occur at a sufficiently high repetition rate to cause the image presented to appear stationary, i.e. without exhibiting flicker to the human eye.

The present invention therefore, provides a real time imaging system which provides a B-scan display equivalent to the shifting of elements along a segmented transducer array in steps of one-half the center-to-center distance between juxtaposed transducer elements. The 123 lines display described above provides an imaging system having greater resolution than heretofore achieved. In an alternative embodiment, the elements 12 are energized in alternating groups of four elements and three elements along the array. Such a system is limited by greater complexity of the logic circuit requirements and is unduly limited in depth of penetration of the acoustic energy signal. For example, to prevent flicker of the display during 123 lines of information during one scan of the array 10, the maximum time between energization necessary to maintain a 50 hertz update rate of the display and a 20 microsecond delay between energizations for permitting logic circuit functions to occur is 144 microseconds. This time is equivalent to a depth of penetration of approximately 10 centimeters in human tissue. In contast in the present embodiment, employing an interlaced display pattern with the group size alternating for each scan of the array 10, penetration to depths in excess of 20 centimeters in human tissue is achievable or twice the depth of that obtained heretofore.

In the described embodiment of the present invention a 64 element array 10 is energized in groups of four and three elements during alternating scans. It will be apparent that arrays comprising other suitable quantities of elements may be used with the limitation that scanning must occur at a sufficiently high rate to avoid the appearance of flicker on the cathode ray tube screen while permitting echo responsive signals from a desired depth in the test object to be received and processed.

While the quantity of elements during alternating scans differs, in the present example by one element, it will be apparent that other quantities of elements may be selected for providing other lateral beam axis shifts. Moreover, the group size may differ in quantity by more than one element.

While there has been described and illustrated a preferred embodiment of the present invention and several modifications have been indicated, it will be apparent to those skilled in the art that further and still other modifications may be made without deviating from the broad principle of the present invention which shall be limited only by the scope of the appended claims.

What is claimed is:

1. A real-time ultrasonic cross-sectional imaging system comprising:
   a segmented transducer array formed of juxtaposed elements;
   means coupled to said array for energizing a selected quantity of juxtaposed elements forming a group for causing each element in said group to simultaneously transmit acoustic energy into an object to be examined and receive echo responsive signals therefrom;
   means coupled to said means for energizing for sequentially shifting said group along said array for effecting a scan of said array, and
   control means coupled to said means for sequentially shifting for providing a different quantity of juxtaposed elements forming a group during alternating scans of said array.

2. A real-time ultrasonic cross-sectional imaging system as set forth in claim 1, each said group being less than the total quantity of juxtaposed elements.

3. A real-time ultrasonic cross-sectional imaging system as set forth in claim 2, said quantity of elements during alternating scans being different by one element.

4. A real-time ultrasonic cross-sectional imaging system as set forth in claim 2, said quantity of elements between alternating scans alternating between an even and an odd quantity of elements.

5. A real-time ultrasonic cross-sectional imaging system as set forth in claim 1, said means for sequentially shifting including a shift register.

6. A real-time ultrasonic cross-sectional imaging system as set forth in claim 5, said means for energizing comprising for each element:
   means for providing trigger pulses;
   first voltage potential means for applying a first potential across such element;
   second voltage potential means coupled in series with switch means for applying a second potential across such element responsive to said trigger pulses and signals from said shift register.

7. A real-time ultrasonic cross-sectional imaging system as set forth in claim 1, said control means including:
   counting means for counting the quantity of transmissions of acoustic energy into the object to be examined for providing a signal indicative of the conclusion of a scan of said array;
   data input means coupled to said counting means for providing responsive to said signal indicative of the conclusion of a scan initial condition signals to said means for sequentially shifting.

8. A real-time ultrasonic cross-sectional imaging system as set forth in claim 7, said initial condition signals being different during alternate scans of said array.

9. A real-time ultrasonic cross-sectional imaging system including in combination:
   a segmented transducer array formed of juxtaposed elements;
   means coupled to said array for energizing a selected group comprising a predetermined quantity of juxtaposed elements for causing each element in said group to simultaneously transmit acoustic energy into an object to be examined and to receive echo responsive signals arising from an acoustic discontinuity in the object;
   means coupled to said means for energizing for sequentially shifting said group of elements along said array in increments of one element for providing a scan of said array;
   display means coupled to said array and said means for sequentially shifting for displaying an image of said echo responsive signal;
   the improvement comprising:
   control means coupled to said means for sequentially shifting and said display means for causing during a first scan of said array, said group to include a first predetermined quantity of elements and the display comprising a first set of spaced lines along an axis of the display and for causing during a second scan of said array said group to include a second predetermined quantity of elements and the display during said second scan comprising a second set of spaced lines disposed between said first set of lines for providing interlacing of displays during alternate scans of said array.

10. A real-time ultrasonic cross-sectional imaging system as set forth in claim 9, said first and said second quantity of elements being less than the elements forming said array.

11. A real-time ultrasonic cross-sectional imaging system as set forth in claim 10, said first quantity of elements and said second quantity of elements being different.

12. A real-time ultrasonic cross-sectional imaging system as set forth in claim 11, said first quantity of elements and said second quantity comprising respectively an even and an odd quantity of elements.

13. A real-time ultrasonic cross-sectional imaging system as set forth in claim 11, said first quantity and said second quantity being different by one element.

14. A real-time ultrasonic cross-sectional imaging system as set forth in claim 9, said control means comprising:
   counter means for counting in units of two and providing an output signal indicative of the quantity of acoustic energy transmissions into the object during a scan of said array;
   logic circuit means coupled to said counter means for causing said count signal to be increased by one unit during alternate scans of said array, and
   step generator means coupled to said counter means for receiving said output signal and causing a line to be traced along said display at a location responsive to said output signal corresponding to each acoustic energy transmission to interlace the display during alternate scans of said array.

15. A real-time ultrasonic cross-sectional imaging system as set forth in claim 14, and data input means coupled to said means for sequentially shifting for causing the quantity of juxtaposed elements in said group to alternate during alternate scans of said array.

16. The method of providing an ultrasonic pulse-echo real-time image comprising the steps:
   providing a segmented transducer array formed of a plurality of juxtaposed elements;
   energizing a first predetermined quantity of juxtaposed elements forming a first group of elements for causing said elements to transmit an ultrasonic search beam into an object and providing subsequently echo responsive signals arising from an acoustic discontinuity in the object;
   shifting said first group along said array by incrementally stepping said group along said array from one end to the opposite end whereby to complete one scan;
   energizing a second predetermined quantity of juxtaposed elements forming a second group of elements for causing said elements to transmit an ultrasonic search beam into the object and providing subsequently echo responsive signals arising from an acoustic dicontinuity in the object;
   shifting said second group along said array by incrementally stepping also said second group along said array from one end to the opposite end whereby to complete another scan, and
   alternating said one and said another scan.

17. The method of providing an ultransonic pulse-echo real-time image as set forth in claim 16 and displaying the echo responsive signals obtained during the respective scans.

18. The method of providing an ultrasonic pulse-echo real-time image as set forth in claim 17, said display comprising a first line raster responsive to said one scan and a second line raster interlaced with respect to said first raster responsive to said another scan.

19. The method of providing an ultrasonic pulse-echo real-time image as set forth in claim 17, said display being a B-scan presentation.

20. The method of providing an ultrasonic pulse-echo real-time image as set forth in claim 16, said first quantity being different from said second quantity.

21. The method of providing an ultrasonic pulse-echo real-time image as set forth in claim 20, said first quantity and said second quantity being different by one element.

22. The method of providing an ultrasonic pulse-echo real-time image as set forth in claim 20 said first group and said second group comprising respectively an even and an odd quantity of transducer elements.

23. The method of providing an ultrasonic pulse-echo real-time image as set forth in claim 16, said incrementally stepping comprising stepping said respective groups by one element.

24. A real-time ultrasonic cross-sectional imaging system including in combination:
- a segmented transducer array formed of juxtaposed elements;
- means coupled to said array for energizing a selected group comprising a predetermined quantity of juxtaposed elements for causing each element in said group to simultaneously transmit acoustic energy into an object to be examined and to receive echo responsive signals arising from an acoustic discontinuity in the object;
- means coupled to said means for energizing for sequentially shifting said group of elements along said array for providing a scan of said array;
- cathode ray tube display means coupled to said array and said means for sequentially shifting for displaying on a screen of said tube an image of said echo responsive signal;

the improvement comprising:
- means coupled to said means for sequentially shifting and to said display means for causing each scan of said array to appear on the screen of said tube as a set of spaced lines along an axis of said screen and two successive scans to provide an interlaced pattern of said lines.

* * * * *

UNITED STATES PATENT AND TRADEMARK OFFICE
CERTIFICATE OF CORRECTION

PATENT NO. : 4,064,741
DATED : December 27, 1977
INVENTOR(S) : CHARLES A. REYNOLDS It is certified that error appears in the above-identified patent and that said Letters Patent are hereby corrected as shown below:

Column 1, line 49, "transducer" should be --Transducer--.

Column 2, line 3, "arrangements" should be --arrangement--;

line 34, after "distance" insert --between--;

line 40, after "quantity" insert --of--.

Column 3, line 20, "alternatively" should be --alternately--.

Column 4, line 2, "thrid" should be --third--;

line 25, "Moreoever" should be --Moreover--.

Column 5, line 12, "time-again" should be --time-gain--.

Column 7, line 44, after "object" insert --along--.

Signed and Sealed this

Eighteenth Day of April 1978

[SEAL]

Attest:

RUTH C. MASON
Attesting Officer

LUTRELLE F. PARKER
Acting Commissioner of Patents and Trademarks